United States Patent [19]
Brown

[11] Patent Number: 6,037,168
[45] Date of Patent: Mar. 14, 2000

[54] MICROBIOLOGICAL ASSEMBLY COMPRISING RESEALABLE CLOSURE MEANS

[75] Inventor: James F. Brown, Clifton, Va.

[73] Assignee: Cytonix Corporation, Beltsville, Md.

[21] Appl. No.: 09/001,466

[22] Filed: Dec. 31, 1997

[51] Int. Cl.$^7$ ................................................ C12M 3/00
[52] U.S. Cl. ................................. 435/288.3; 435/288.4; 435/305.1; 435/305.2; 435/305.3; 435/305.4
[58] Field of Search ............................ 435/288.3, 288.4, 435/305.1, 305.2, 305.3, 305.4

[56] References Cited

U.S. PATENT DOCUMENTS

| | | | |
|---|---|---|---|
| 3,726,764 | 4/1973 | White | 195/127 |
| 3,745,091 | 7/1973 | McCormick | 195/139 |
| 3,891,327 | 6/1975 | Welch | 356/244 |
| 4,447,140 | 5/1984 | Campbell et al. | 350/534 |
| 4,599,314 | 7/1986 | Shami | 435/287 |
| 4,705,705 | 11/1987 | Bross | 438/13 |
| 4,722,598 | 2/1988 | Ford | 350/536 |
| 4,818,623 | 4/1989 | Hozumi et al. | 428/447 |
| 4,853,262 | 8/1989 | Horie et al. | 428/13 |
| 4,911,782 | 3/1990 | Brown | 156/633 |
| 5,192,503 | 3/1993 | McGrath et al. | 422/57 |
| 5,200,152 | 4/1993 | Brown | 422/102 |
| 5,417,576 | 5/1995 | Hill | 435/299 |
| 5,436,033 | 7/1995 | Mino et al. | 437/498 |
| 5,503,803 | 4/1996 | Brown | 422/102 |
| 5,518,925 | 5/1996 | Tyndorf et al. | 435/305.2 |
| 5,533,759 | 7/1996 | Jeffers | 283/70 |
| 5,536,982 | 7/1996 | Mino et al. | 307/400 |
| 5,543,224 | 8/1996 | Sakai et al. | 428/409 |
| 5,556,618 | 9/1996 | Ando et al. | 424/78.08 |
| 5,558,809 | 9/1996 | Groh et al. | 252/62.54 |
| 5,565,717 | 10/1996 | Lewiner et al. | 307/400 |
| 5,571,721 | 11/1996 | Turner | 435/305.1 |
| 5,661,029 | 8/1997 | Self et al. | 435/288.3 |
| 5,682,670 | 11/1997 | Bell et al. | 29/609 |

OTHER PUBLICATIONS de Macario, et al., "Multiple Solid–Phase System for Storage of Dry Ready–for–Use Reagents and Efficient Performance of Immunoenzymatic and Other Assays," *Journal of Immunological Methods* 99:107–112 (1987).

Weber–Matthiesen, et al., "Rationalization of In Situ Hybridization: Testing up to 16 Different Probes on a Single Slide," *Cancer Genet Cytogenet* 68:91–94 (1993).

Piazza, et al., "In Situ Immunoassay for the Assessment of *Trypanosoma cruzi* Interiorization and Growth in Cultured Cells," *Acta Tropica* 57:301–306 (1994).

Rosenzvit, et al., "A Simple and Economic Slide Micro–Immunoenzymatic (Micro–SIA) Test for Epidemiological Studies of Tosoplasmosis," *Mem Inst Oswaldo Cruz*, 89(1):47–51 (Jan./Mar. 1994).

Simpson, et al., Determination of [$^3$H]TdR–Labelling Indices of Cultured Cells Grown on Detachable Chamber Slides,: *Cell Tissue Kinet.*, 18:155–157 (1985).

Smith, et al., "Enzyme–Linked Immunosorbent Assay (ELISA) for HIV Antibody by a Glass Slide Technique," *Journal of Immunological Methods*, 136:239–246 (1991).

Tsai, et al., "Cytokine–Induced Differentiation of Cultured Nonadherent Macrophages," *Cellular Immunology* 144:203–216 (1992).

*Primary Examiner*—David A. Redding
*Attorney, Agent, or Firm*—Kilyk & Bowersox, P.L.L.C.

[57] ABSTRACT

A microbiological assembly is provided having a resealable seal between a support and a cover. The support has a surface which includes a patterned layer and defines at least one sample retention well. The cover has a surface which contacts a sealant and the sealant is disposed on at least one of the support and the cover. The sealant is adapted to releasably bond and resealably seal the cover to the support. The sealed assembly minimizes contamination and drying of liquid sample retained by the sample retention well. A method of examining a biological culture is also provided and includes the steps of retaining a biological sample within the sample retention well of the assembly, sealing the cover to the support with the sealant between the sealing surface and the support surface, physically separating the cover from the support surface, and then either resealing the cover or sealing a second cover to the support using the same sealant. Assemblies including magnetic, electrostatic and other resealable seals are also provided.

22 Claims, 6 Drawing Sheets

MICROBIOLOGICAL ASSEMBLY COMPRISING RESEALABLE CLOSURE MEANS

FIELD OF THE INVENTION

The present invention relates to an assembly and a method for using the assembly in biological culture production and examination. The present invention also relates to closure means for biological culture assemblies and methods for using the closure means to seal an assembly used for biological culture production and examination.

BACKGROUND OF THE INVENTION

It is frequently desirable in medical laboratory practice as well as in biological research to grow cells or tissues in particular media and then to examine the resulting growth. This procedure can be carried out by growing cells in one media and then transferring the cells to a microscope slide for optical examination. For example, cells can be grown in tissue culture flasks or bottles or in multi-well (micro-titer) test plates. These multi-well plates are well known and exemplified in U.S. Pat. Nos. 3,540,857 and 3,540,858.

Microtiter plates can be injection molded from polystyrene. Typically, such test plates have been standardized in forms that provide ninety-six depressions or cylindrical wells, each being about 0.66 cm in diameter and about 1.3 cm deep, arranged in a 12×8 regular rectangular array with the wells being spaced about 0.9 cm center to center. A flat lid is employed for covering the plates during incubation. Cell cultures can be incubated in the wells and in-vitro assays can be performed on the cultures.

Microtiter plates offer an advantage over flasks and bottles by allowing for the simultaneous growth of individual cultures and assays. None of these devices, however, provides a flat clear viewing surface for fluorescence and confocal imaging of cells. Therefore, cells from a produced culture are transferred to a glass microscope slide or coverslip for optical viewing. This procedure of growing a culture in one container and transferring the culture or cells therefrom for microscopic viewing has its downfalls in that the cells thus observed are not in their native state. Thus, true in-situ observation does not occur. The transfer procedure also requires an additional manipulative step.

U.S. Pat. No. 3,726,764 to White discloses a chamber attached to a glass slide with a liquid-impermeable seal. A special tool is wedged into the seal to separate the chamber from the glass slide. A problem which has confronted users of typical apparatus as described in U.S. Pat. No. 3,726,764 is that a separate tool to remove the chamber from the slide is not convenient and in spite of the high level of skill and care in separating the chamber and the slide, the potential for not shattering the glass slide is not always assured, and therefore, contamination of the culture on the slide is not assured. Furthermore, although the receptacle may be sealed to the base member, the patent does not disclose a completely liquid-impermeable assembly as there is no provision for sealing the lid 18 onto the assembly.

U.S. Pat. No. 3,745,091 to McCormick discloses an assembly comprising a microscope slide as a base member providing a planar surface and a receptacle formed of upstanding sidewalls and upstanding endwalls. The receptacle is attached to the base by a removable adhesive gasket. Partitions form a unitary structure with the sidewalls and endwalls and define cubical chambers in the receptacle. The receptacle, which can form one to eight cubical chambers, is preferably formed from a transparent organoplastic material, such as polystyrene, polypropylene, polymethacrylate, and the like. The adhesive gasket is made of, for example, an organopolysiloxane elastomer. A cover is used to seal the device. Cells and liquid media are placed in the cubicals, covered, and incubated. The liquid media is removed from the chamber and the receptacle removed from the base. The cell culture growth on the base glass is then treated as desired and examined microscopically. Unfortunately, this device has many disadvantages, for example, the gasket is often difficult to remove resulting in breakage of the glass slide, and the size of the cubicals are relatively large requiring a minimum of 100 $\mu$l liquid. This type of device is currently sold as Lab-Tek Chambered Coverglass Products by Nunc, Inc, Naperville, Ill. Use of this type of device is described more fully by Simpson et al. (1985), Tsai et al. (1992), and Piazza et al. (1994).

Current molecular biology technology which now allows for the detection of a single copy of a specific gene or gene sequence has permitted the use of smaller and smaller numbers of cells for conducting biological research. Thus the number of cells required for a variety of biochemical assays, such as cell growth and attachment studies, cell differentiation studies, in-situ hybridization, and immunohistochemical procedures, has been greatly reduced. The reduction in assay size for these biological assays leads to a reduction in the use of expensive reagents and offers the opportunity to conduct more assays simultaneously.

Glass microscope slides with one or more reaction fields which are bounded by a hydrophobic surface coating are used for a wide variety of biological assays. These devices which are available from Cell-Line Associates, Newfield, N.J., Erie Scientific, Rye, N.H. and Precision Scientific, Madison, Wis., and are described in U.S. Pat. No. 4,705,705 to Bross. Typically, these glass slides have 5–10 mm wells which can hold from 20 to 100 $\mu$l of fluid. The wells contain considerably less fluid than the Lab-Tek or Super Cell devices thus producing a considerable savings in cost of reagents. In addition, the reduction in size allows many more wells to be tested simultaneously. Slides can easily contain 16–64 wells. Cells can be transferred from cell culture devices to the wells of the slide for assaying and microscopic viewing. Cells can either be in suspension or fixed to the surface of the slide. Subsequently, reagents may be added to the wells and held in place by forces of surface tension. These slides are used for numerous types of investigations, namely:

1. morphological investigations of cells following fixing and staining, in a manner similar to the normal smear techniques and cytocentrifuging;

2. incubation of cells with various antibodies against cell membrane antigens for the identification of specific cell populations, with subsequent visualization of reaction by means of antibody labeling with enzymes, fluorescent dyes or gold particles;

3. detection of intracellular antigens by means of labeled antibodies, following drying and fixing of the cells;

4. detection by reactions of the cells with particles such as bacteria, latex particles, acrylic particles etc., and with substances such as dyes, toxins, and lectins;

5. performance of cytochemical reactions for the detection of cellular enzymes; and 6. coating and processing of tissue sections for pathological examination.

For investigations (1)–(5) above it would be a considerable advantage to grow cells directly on these devices in order to perform true in-situ assays on small number of cells and to eliminate the step of transferring cells from a different growth environment, the solution to which problem the present invention addresses. All of the above investigations (1)–(6) may have single or multiple incubations steps.

A recent modification of the Lab-Tek device replaces the aforementioned gasket with an acrylic pressure sensitive adhesive, as described in U.S. Pat. No. 5,571,721 to Turner, which discloses a slide and a cover adhered to the slide with the acrylic adhesive. According to the patent, substantially all of the acrylic adhesive remains attached to the cover when the cover is removed from the slide. A common problem which has confronted users of apparatus as described in U.S. Pat. No. 5,571,721 is that the seal provided by the acrylic adhesive between the slide and the cover is neither leak-proof, liquid impermeable, nor resealable. Furthermore, because the adhesive is removed with the cover, if a more permanently storable container is to be provided, as, for example, when a coverslip is placed over the culture and glued to the slide along the periphery of the coverslip, additional adhesive must be delicately placed on the slide, carefully surrounding the culture. Furthermore, a special device is needed to remove the receptacle and pressure sensitive adhesive from the glass slide, and removal of the receptacle still results in occasional breakage of slides. After separation from the slide, the receptacle cannot be resealed to the slide to form a leak-proof seal. Devices of this type are known as Super Cell Culture Slides, manufactured by Erie Scientific, Rye, N.H., and are sold with 1 to 16 individual chambers.

In addition to the aforementioned problems, none of the foregoing mentioned assemblies provides a protective cover sealed to a base wherein the cover can be temporarily removed from the base to gain access to a growing or grown culture, and then resealably reattached to the base.

With the increased emphasis on the efficacy of medical and research products, a need exists for an improved apparatus for effectively and efficiently carrying out biological culture production. The improved apparatus would better protect the person carrying out the procedure and would be simple and inexpensive to manufacture as compared to currently available devices.

Another desired feature for a microbiological assembly is the ability of the assembly to preserve a biological culture for long-term examination of the culture or for use as a reference or control. Cultures are sometimes preserved by being sealed within an anaerobic environment free from contamination and drying. For example, a permanent coverslip may be adhered or otherwise attached to a slide having a culture grown thereon with the coverslip covering the culture. A permanent adhesive may be used to seal the culture between the slide and coverslip. A coverslip may be mounted over a specimen on a slide by bonding the coverslip to the slide by means of a cement adhesive, natural or synthetic resin, or a photosensitive material such as an acrylate that solidifies under UV light.

In assemblies comprising removable compartments or covers, long-term preservation of a culture grown on an assembly support would heretofore require removing the compartment or cover, applying a permanent adhesive to either the assembly support or a coverslip, and permanently adhering the coverslip to the support with the culture therebetween. Great care must be taken so as not to contaminate the culture with the adhesive and so as to completely seal the culture from all sides. Furthermore, the permanent adhesive makes it difficult, if not impossible, to later remove the coverslip and gain future access to the culture. A need exists for a simpler and safer way to seal a culture for long-term preservation, examination, study and reference.

It would be desirable to provide a microbiological assembly which can be converted from a culture growth assembly to a microscopic examination assembly without the need to perform a manipulative step of applying an adhesive for a coverslip after a culture-growth cover is removed.

SUMMARY OF THE INVENTION

The present invention provides a microbiological assembly which is covered with a resealable cover that reduces evaporation of costly reagents, minimizes assay contamination, and eliminates the need to store such slides in humid incubation chambers. The present invention also provides a microbiological or chemical reaction assembly having a resealable closure means that is used for sealing a first cover and then sealing a second cover after the first cover is released from the closure means.

It is an object of the present invention to provide a multi-chambered device for growing cells and performing assays on a flat planar surface.

It is a further object of the present invention to provide a multi-chambered device for growing cells and conducting assays using very small volumes.

It is a further object of the present invention to provide a multi-chambered device for growing cells and performing assays which has a resealable cover of any of various dimensions.

It is a further object of the present invention to provide a multi-chambered device for growing cells and performing assays wherein the device may have a permanent cover of any of various dimensions.

It is a further object of the present invention to provide a multi-chambered device for growing cells and performing an assay wherein the device has a cover which attaches to a support by means of a pressure sensitive adhesive which is resistant to laboratory chemicals used for the cell growth and the assay.

It is a further object of the present invention to provide a multi-chambered device for growing cells and performing an assay wherein the device has a cover which attaches to a support by means of a pressure sensitive adhesive which is resistant to laboratory chemicals used in the cell growth and the assay, and, when in contact with a hydrophobic surface, forms a virtually leak-proof seal.

It is yet a further object of the present invention to provide a multi-chambered device for growing cells and conducting assays which is both inexpensive and disposable.

It is a further object of the present invention to provide a miniature biological assembly having a closure means on a support wherein the closure means can resealably seal a cover to the support and then more permanently seal the same or a different cover to the support.

According to embodiments of the present invention, a device containing one or more miniature biological reaction chambers is provided which may hold from about 1 $\mu$l to about 1 cl of fluid. According to some embodiments of the invention, the assembly preferably has a substantially planar bottom surface and/or a support thickness of from about 10 $\mu$m to about 200 $\mu$m.

The present invention provides a microbiological assembly comprising a support, a resealable closure means, and a cover. The support has a support surface which may include a patterned layer. The support surface preferably has one or more sample retention means formed therein or thereon. The cover preferably has a sealing surface for contacting the closure means and the resealable closure means is preferably disposed on at least one of the support surface and the sealing surface of the cover. The resealable closure means or resealable sealant is adapted to releasably bond and resealably seal the cover to the support surface.

According to embodiments of the invention, when the cover is sealed to the support surface a leak-proof sealed assembly is provided having the sample retention means contained therein. The sealed container eliminates or at least minimizes environmental contamination, drying of liquid sample and evaporation of media retained by the sample retention means or in the assembly. Since the cover can be removed and resealed multiple times, media, reactants, wastes and products can be easily replenished or removed. According to embodiments of the invention, cells may be grown directly on the assembly. According to embodiments of the invention wherein the assembly comprises a chemical reactor chamber, chemical reactants and/or products can be easily removed or replenished multiple times.

The closure means may comprise: a resealable pressure sensitive adhesive; a magnetic force-generating material, for example, a printed magnetic ink layer; or an electric force-generating material, for example, an electret material; or other resealable sealing means.

The present invention also provides a method of examining a biological culture including retaining a biological sample within a sample retention means of an assembly according to the invention, sealing the cover to the support surface of the assembly with the closure means between the sealing surface and the support surface, physically separating the cover from the support surface, and then either resealing the cover to the support surface or sealing a coverslip to the support surface, using the same resealable closure means.

BRIEF DESCRIPTION OF THE DRAWINGS

Further benefits and advantages of the invention will become apparent with reference to the accompanying drawings, wherein.

DETAILED DESCRIPTION OF THE INVENTION

Figure 1:
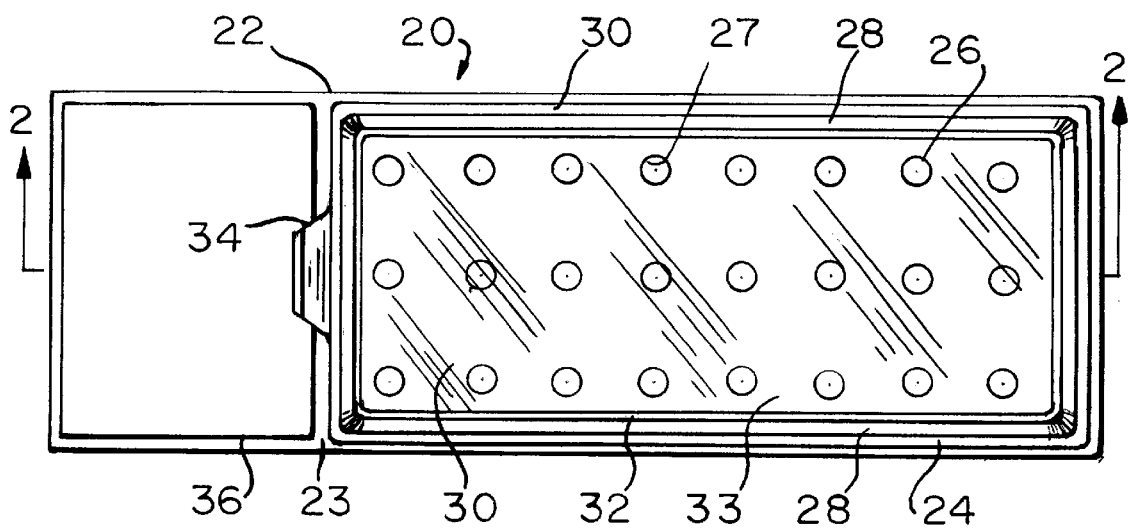
FIG. 1 is a top plan view of a microbiological assembly according to embodiments of the present invention.

According to embodiments of the present invention, a microbiological assembly is provided comprising a support, resealable closure means, and a cover. The support has a support surface and sample retention means. The support may comprise a patterned layer. The cover has a sealing surface for contacting the resealable closure means, and the resealable closure means is disposed on at least one of the support surface and the sealing surface of the cover. The resealable closure means is adapted to releasably bond and resealably seal the cover to the support surface.

The closure means seals the cover to the support surface to form a substantially leak-free sealed container having sample retention means contained therein. The sealed container minimizes contamination and drying of liquid sample and liquid media in the assembly. The closure means preferably forms a solvent-resistant seal which permits only the exchange of gases between the sample retention means and the outside atmosphere. Thus a substantially contaminant-free atmosphere for growing cells and for reducing evaporation of culture media is produced.

The cover can be lifted to replenish media or to add selective ingredients. Once cells have reached a certain growth phase, the cover can be easily and smoothly removed so that the cells can be examined, in a natural state, directly on the slide. Reagents can be added to hydrophobic delimited reaction areas and the cover can be replaced in order to incubate reagents used in various biological assays.

According to embodiments of the invention, an assembled assembly is provided wherein the cover is releasably and resealably sealed to the support surface and the closure means is disposed between the cover and the support surface. According to such embodiments, the closure means seals the cover to the support surface and is adapted to reseal the cover to the support surface after physical separation of the cover from the support surface.

According to some embodiments of the invention, the closure means comprises a patterned layer of an adhesive material disposed on the support surface. The patterned layer of adhesive material remains resealable, substantially intact, and adhered to or disposed on the support surface after adhering the cover to the support surface and then physically separating the cover from the support surface.

According to some embodiments of the invention, the closure means comprises a patterned layer of an adhesive material disposed on the sealing surface of the cover. The patterned layer of adhesive material remains resealable, substantially intact, and adhered to or disposed on the sealing surface after adhering the cover to the support surface and then physically separating the cover from the support surface.

According to some preferred embodiments of the invention, the closure means comprises an adhesive material disposed on at least one of the support surface and the sealing surface of the slide, but that remains partially adhered to the support surface and partially adhered to the sealing surface of the cover upon removal of the cover from the support. This desirable cohesive failure of the adhesive layer is advantageous according to some embodiments of the invention.

Preferably, the cohesively failed split adhesive layer according to the invention forms a substantially uniform and continuous adhesive patterned layer on the support surface and a substantially uniform and continuous adhesive patterned layer on the sealing surface of the cover. According to some embodiments, from about 10% by thickness to about 90% by thickness of the adhesive layer remains bonded to the support surface in a patterned layer and from about 10% by thickness to about 90% by thickness of the adhesive layer remains bonded to the sealing surface of the cover in a patterned layer. According to some embodiments, from about 30% by thickness to about 70% by thickness of the adhesive layer remains bonded to the support surface in a patterned layer and from about 30% by thickness to about 70% by thickness of the adhesive layer remains bonded to the sealing surface of the cover in a patterned layer. According to some embodiments, the about 50% by thickness of the adhesive layer remains bonded in a pattern to the support surface and about 50% by thickness of the adhesive layer remains bonded in a pattern to the sealing surface of the cover. According to embodiments of the invention, each of the adhesive layer portion remaining on the support surface and the adhesive layer portion remaining on the sealing surface of the cover may be used independently as a resealable closure means. A preferred adhesive for desired cohesive failure applications comprises L-9186 Fluorinert™ liquid available from 3M.

According to some embodiments of the invention, the closure means comprises a pressure sensitive adhesive. According to some embodiments of the invention, the closure means preferably comprises an adhesive selected from the group consisting of fluorosilicone pressure sensitive adhesives, fluoroacrylate pressure sensitive adhesive, silicone pressure sensitive adhesives, and oligomeric pressure sensitive adhesives. Other pressure sensitive adhesives may be used provided the adhesive is resealable and provides a liquid-impermeable seal, is non-toxic to the biological material employed or cultured in the assembly, and does not act as a source of growth for undesirable microorganisms. A preferred pressure sensitive adhesive comprises about 90% by weight FX-189 Fluorinert liquid available from 3M mixed with about 10% by weight low $T_g$ isooctyl acrylate monomer and a catalytically effective amount of a UV-curing catalyst, which is partially UV-cured to a printable consistency, printed, and subsequently substantially fully cured.

Other preferred pressure sensitive adhesive materials that can be used according to the present invention include adhesives described in U.S. Pat. No. 5,482,991 to Kumar et al. which discloses non-aqueous dispersions of copolymers of acrylic monomers prepared in the presence of vinyl-substituted fluoroalkylsiloxane and a macromonomer stabilizer. Other preferred pressure sensitive adhesives include pentafluoropropyl acrylate adhesives and copolymers of vinylidene fluoride and hexafluoropropylene.

According to some embodiments of the invention, the closure means comprises a pressure sensitive adhesive that remains bonded or adhered to a patterned layer fixed on the sealing surface of the support rather than being removed with the cover. According to such embodiments, the closure means may then be reused after the cover is removed, to adhere a more permanent cover, for example, a microscope slide coverslip, to the support. According to some embodiments of the invention, a culture or reaction product produced on a support under a cover may be treated, for example, stained, after the cover is removed, and the closure means may then be reused to adhere a microscope coverslip for preserving and examining the product.

If a pressure sensitive adhesive is used as the closure means, it is preferably solvent-resistant and non-toxic. Rinsing or soaking the device in various laboratory chemicals used for employment of the assembly should not substantially alter the ability of the pressure sensitive adhesive to exhibit a greater affinity to one of the cover and the support and releasably and resealably seal to the other of the cover and the support. Therefore, according to embodiments of the invention wherein the closure means is a pressure sensitive adhesive which remains attached to the support, the support with the pressure sensitive adhesive thereon can be dipped in ethanol for sterilization without the need to worry about destroying the sealability or resealability of the adhesive.

According to embodiments of the invention wherein an assembly is used as a chemical reaction assembly, the adhesive is preferably inert to, and does not affect the properties of, reactants and products of a reaction carried out in the assembly.

If the closure means comprises a pressure sensitive adhesive, it can initially be attached to the support, the cover, or both. Attachment of the cover may comprise direct contact of a pressure sensitive adhesive with both the cover and the hydrophobic surface of the support, to provide a leak-proof barrier and to facilitate gentle removal of the cover. The thickness of the adhesive layer may be from about 10 microns to about 1 cm. Thicknesses of from about 0.1 mm to about 1.0 mm are preferred according to some embodiments of the invention. Adhesive layers which are additionally useful as spacers may be up to about 1 cm thick and may preferably comprise a hydrophobic material.

According to some embodiments of the invention, the closure means may preferably comprise a resealable adhesive which, after sealing a first cover to the support and then removing the first cover, can be used to permanently seal the first cover or a second cover to the support. For example, the closure means may comprise a pressure sensitive adhesive containing UV-curable monomers dispersed therein, wherein the UV-curable components are UV-cured after a first cover is sealed to the closure means and removed and then a second cover is sealed to the closure means. The closure means may comprise a formulation comprising first and second curing mechanisms, wherein the first curing mechanism is employed to provide a resealable pressure sensitive adhesive closure means and the second mechanism is subsequently employed to provide a substantially more permanent closure means. An example of such an adhesive comprises a fluorosilicone copolymerized with a glycidyl acrylate and also a heat or UV-sensitive catalyst for opening the epoxy ring for subsequent more permanent adhesion. Another example of such a dual curing formulation is described in U.S. Pat. No. 5,578,683 to Coch which discloses a crosslinkable pressure sensitive adhesive graft polymer formed of an acrylic backbone and a crosslinkable reactive moiety.

According to some embodiments of the invention, the closure means comprises a magnetic material disposed on at least one of the sealing surface of the cover and the support surface. The magnetic material may also be applied to the other of the support and the cover or a magnetically attractive material may be applied to one of the support and the cover. Preferred magnetic materials for sealing applications include printable magnetic inks, for example, inks containing magnetic particles as described in U.S. Pat. Nos. 5,533,759 to Jeffers and 5,682,670 to Bell et al., which patents are incorporated herein in their entireties by reference. According to embodiments of the invention, a magnetic material is used which comprises a printable ink containing magnetic particles, or a resin or polymer containing magnetic particles. Preferably, the ink, resin or polymer is cured, dried or hardened in the presence of a magnetic field such that the magnetic particles therein are aligned during curing, drying or hardening to form a magnetic structure.

According to embodiments of the invention wherein the closure means comprises a magnetic material, the material may be applied and bonded to a peripheral or marginal region of the support or the cover. The magnetic material, or a material that exhibits an attraction to a magnetic field, for example, an iron layer, is applied and bonded to a peripheral or marginal region of the other of the support and the cover. Due to the magnetic attraction between the material applied on the support and the material applied on the cover, the support and cover may be sealed together. According to some embodiments of the invention, the magnetic material comprises a hardened resin or polymer having magnetic particles dispersed throughout wherein the resin or polymer exhibits at least some elasticity, and the elastic nature of the material enables a leak-proof seal to be formed when the material on the support and the material on the cover are magnetically bound together. Preferably, the magnetic material forms a resealable seal between the sealing surface of the cover and the sealing surface of the assembly support, and the seal is liquid-impermeable, non-toxic to sample material employed or cultured in the assembly, does not act as a source of growth for undesirable microorganisms, and exhibits excellent temperature stability and low moisture regain. A preferred magnetic material which can be used comprises a neodymium-iron-boron magnetic powder dispersed in a slow curing, low viscosity liquid epoxy resin system, as described in U.S. Pat. No. 5,682,670 to Bell et al. According to embodiments of the invention wherein an assembly is used as a chemical reaction assembly, the magnetic material and/or magnetically attractive material is preferably inert to, and does not affect the properties of, reactants and products of a reaction carried out in the assembly.

According to some embodiments of the invention the closure means comprises a material that has been hardened in the presence of an electric field and holds a charge, for example, a meltable plastic having a dipole moment. Closure means of this type include electret materials, particularly polymer electrets, for example, electrets as described in U.S. Pat. Nos. 5,436,033 to Mino et al., 5,536,982 to Mino et al., 5,543,224 to Sakai et al., 5,556,618 to Ando et al., 5,558,809 to Groh et al., and 5,565,717 to Lewiner et al., which are all incorporated in their entireties herein by reference. According to embodiments of the invention, the electret may comprise a polyolefin, polypropylene, polyethylene, polycondensate, polyamide, polyester, polycarbonate, polyarylate, polyacrylate, polyacetal, polyimide, cellulose ester, polystyrene, fluoropolymer, polyphenylenesulfide, or mixtures thereof. Combinations of polymers may also be used, for example, copolymers and polymer blends. General material requirements and performance characteristics of suitable electret polymers are also described, for example, in G. Sessler, *Topics in Applied Physics,* Vol. 33: "Electrets", Springer Verlag, London, 1987. Fluoropolymers are preferred according to some embodiments of the invention, for example, polytetrafluoroethylene (PTFE) and perfluorinated ethylene/propylene copolymer (PFEP).

Characteristics of preferable electret polymers according to some embodiments of the invention include long-term charge stability as well as resistance to humidity and chemicals. Preferably, the electret comprises a polymer which, when applied to at least one of the sealing surface of the cover and the sealing surface of the assembly support, provides a resealable seal that is liquid-impermeable, non-toxic to sample material employed or cultured in the assembly, does not act as a source of growth for undesirable microorganisms, and exhibits excellent temperature stability and low moisture regain. According to embodiments of the invention wherein an assembly is used as a chemical reaction assembly, the electret material is preferably inert to, and does not affect the properties of a reaction or reactants or products of a reaction carried out in the assembly.

Other resealable closure may also or instead be used according to embodiments of the present invention. For example, frictional-fit or other mechanical sealing means may be used to resealably seal a cover to an assembly support. According to some embodiments of the invention, a slightly tapered engagement may be provided between an engaging lip or rim of a cover and a protruding ridge or recessed groove formed or provided on or in a support. Rigid and/or flexible elastomeric fits or engagements may also or instead be used to resealable seal the cover to the support. A cover-engaging feature on a support may be provided by injection molding the support or by applying a raised or recessed feature to a substantially planar support, for example, a patterned ridge of a silicone, fluorosilicone or acrylic material may be formed on a microscope slide. According to some embodiments of the invention, a very inexpensive support comprising an injection molded unitary plastic part may be provided, for example, an injection molded polystyrene or PTFE support. A single physical closure means feature such as a ridge or groove may be provided around the periphery of the sample retention containing portion of the assembly, or individual features may be provided around each sample retention means.

Resealable closure means comprising a raised physical feature such as a ridge may also be used to provide added stiffness and integrity to the support, for example, when the support comprises a thin microscope slide coverslip having a raised ridge of a patterned plastic material applied to the top surface thereof.

Other resealable closure means that may be employed according to embodiments of the present invention include engagements including O-rings or flexible gasket materials, leur fittings, hook and loop fastener materials particularly hydrophobic hook and loop fastening materials, zip-lock resealing means such as resealable plastic bag closure means, and other physical feature sealing means which provide a resealable seal, is non-toxic to the biological material employed or cultured in the assembly, and does not act as a source of growth for undesirable microorganisms.

Preferably, the closure means provides a resealable liquid-impermeable seal. More preferably, the closure means provides a resealable seal that is leak-proof to aqueous media and more preferably leak-proof to liquid media. Preferably, the closure means provides a resealable seal that is substantially leak-free and more preferably completely leak-free.

According to some embodiments of the invention, the closure means may comprise a combination of the aforementioned closure means, or a combination of a closure means and a sealing means. For example, the closure means may comprise (1) a pressure sensitive adhesive and a frictional engagement between the cover and the support, (2) a pressure sensitive adhesive surrounding a layer of extremely hydrophobic non-adhesive material, or (3) a frictional-fit engagement surrounding a patterned layer of extremely hydrophobic material.

The closure means, whether a resealable, substantially leak-proof pressure sensitive adhesive layer, a magnetic-loaded material, an electret material, or another resealable means, or combinations or closure means or combinations of closure and sealing means, may be applied, mounted or formed directly to or on the surface of the support material or the cover material, or the closure means may be applied to a patterned layer disposed on at least one of the support and the sealing surface of the cover. The patterned layer may comprise a printed ink, for example, a hydrophobic printed ink. According to embodiments of the invention, a printed layer of hydrophobic ink may be used on at least one of the support sealing surface and the cover sealing surface to control the release or adhesion of the closure means to the printed pattern on the surface.

According to embodiments of the invention, the support may comprise a patterned layer of a material, for example, a hydrophobic ink coating or die-cut layer, that exhibits a greater bond or adhesion to the closure means than to the opposite sealing surface of the cover. Thus, the closure means remains attached to the patterned layer on the support when the cover is removed from the assembly.

The patterned layer may comprise a printed layer of printable ink. Printable formulations for printing a patterned layer may comprise or consist essentially of a polymerization product of a fluoroalkyl ethylenically unsaturated monomer having a terminal trifluoromethyl group and a carbon chain length of from 3 to 20 atoms, preferably from 6 to 12 carbon atoms in length, and more preferably from 8 to 10 carbon atoms in length. In particular, polymerization products of fluoroalkyl methacrylates are preferred. According to some embodiments of the invention, polymerization products of perfluorohexyl methacrylate, perfluoroheptyl methacrylate, perfluorooctyl methacrylate, perfluorononyl methacrylate, perfluorodecyl methacrylate, perfluoroundecyl methacrylate or perfluorododecyl methacrylate, and mixtures thereof, are preferred. Acrylates of such perfluoroalkyls are also preferred. According to one particularly preferred embodiment, the polymer printed coating consists essentially of a polymerization product of perfluorooctyl methacrylate.

Exemplary materials for making the patterned layers of the present invention include formulations comprising, or polymers of, PerFluoroCoat and FluoroPel, both available from Cytonix Corporation, the fluorinated materials FC-722, FX-13, FX-14, FX-189, L-9187, L-9186, Fluorel™ FC 2174 and Fluorel™ FC 2181, all available from Commercial Chemicals Division, 3M, St. Paul, Minn., silastic fluorosilicone rubbers from Dow Corning STI identified as LS-2249U, LS-2332U, LS-2840 and LS-2860, fluorinated materials from DuPont including materials traded under the name ZONYL, and non-fluorinated materials which provide a patterned layer exhibiting sample restraining properties and which are non-toxic to sample material employed or cultured in the assembly, does not act as a source of growth for undesirable microorganisms, and exhibits excellent temperature stability and low moisture regain.

The printable formulation for the patterned layer may comprise a fully fluorinated non-branched fluorocarbon having a carbon chain length of 8 to 20 carbon atoms. Perfluorinated fluorocarbon solvents are preferred according to some embodiments of the invention, for example fluorinated solvents including the Fluorinert® line of fluorinated solvents, FC-40, FC-70 and FC-71, all from the Commercial Chemicals Division, 3M, St. Paul, Minn. Other fluorinated solvents which may be used include Vertrel® XF ($C_5H_2F_{10}$) or Freon TF from DuPont, Wilmington, Del., the fluorinated polyethers HT70, HT85, HT90, HT100, HT110, HT135, HT200, HT230, HT250 and HT270, and the perfluorinated polyethers sold as GALDEN, all from Ausimont USA, Inc.

According to some embodiments of the invention, a patterned layer of an oleophobic, hydrophobic/oleophobic, hydrophilic, porous, semi-permeable or permeable material, or a layer having different regions or paths of different materials, may be provided on at least one of the support, the cover, or a coverslip. A patterned layer may be employed that defines channels, microchannels, pathways or reservoirs.

According to embodiments of the invention, the support may be provided with a patterned layer comprising a layer of die-cut material, for example, a foam material. The die-cut layer may be used to define sample retention wells, or to space a cover or coverslip from a sample retained on the support. If a die-cut layer is employed, it may be bonded to the support, the cover or a coverslip with a permanent adhesive, for example, a UV-curable or heat-curable resin.

According to embodiments of the invention wherein a patterned layer is provided on at least one of the support, the cover or a coverslip, the patterned layer preferably is liquid-impermeable, non-toxic to sample material employed or cultured in the assembly, does not act as a source of growth for undesirable microorganisms, and exhibits excellent temperature stability.

The support, cover and coverslip may preferably be fabricated of soda glass which has been cleaned to remove oils, greases, surfactants, abrasives or other materials inhibitory to biological growth. Other materials that may be used for the support, cover and coverslip include sintered alumina, organoplastics such as polycarbonate and polymethylmethacrylate, polyolefins, polyamides, polyesters, silicones, polyurethanes, epoxies, acrylics, polyacrylates, polyesters, polysulfones, polymethacrylates, polycarbonate, PEEK, polyimide, polystyrene, and fluoropolymers such as PTFE Teflon®, FEP Teflon®, Tefzel®, poly(vinylidene fluoride), PVDF, and perfluoroalkoxy resins. Glass products including silica glass are preferred for the support and coverslip according to some embodiments of the invention.

Ceramic, oxide or metal surfaces can be used for the support according to embodiments of the invention as can surfaces of glass, silicon, silicon compounds or ceramics that have or have not been primed with silane containing materials or other adhesion promoting materials. Supports having surfaces that have been pre-coated with epoxies, silicones, urethanes, acrylics, or other materials can also be used.

The support may comprise an anti-fog coating or a printed or patterned coating. The support may be provided with a moisture retention means, for example, a wick or porous structure. According to some embodiments of the invention, the support may comprise a hydrophilic material. The support may comprise a filter, membrane or foil material. The support may be flat or formed. According to embodiments of the invention, the support may include a region provided with a markable coating.

The cover preferably comprises a plastic material, for example, a polyolefin. The cover may be made by any of a variety of methods, including injection molding. The cover may be transparent, selectively transparent, opaque, or selectively opaque to UV light. The cover may comprise an anti-fog coating or a printed or patterned coating. The cover may be provided with a moisture retention means, for example, a wick or porous structure. According to some embodiments of the invention, the cover is extremely hydrophobic. According to some embodiments, the cover has a sealing surface which exhibits a surface energy of from about 5 to about 40 dynes/cm, for example, from about 5 to about 35 dynes/cm. According to embodiments of the invention, the surface energy of the sealing surface of the cover is less than the surface energy of the sealing surface of the support. According to some embodiments of the invention, the cover may comprise a filter, membrane or foil material. The cover may be flat or formed. The cover may extend over the edge of the support or the cover may have a sealing surface that fits within the surface area of the support.

The cover may have a flat top wall and a depending peripheral skirt which extends from the perimeter of the flat top wall. The cover may be designed to fit over all sample retention means on or in the support. Because planar coverslips placed directly on a sample can damage cell structure by trapping air bubbles or during removal of the coverslip, a coverslip with a slightly raised lip (of about 1 mm to about 5 mm) could alleviate this problem, or a peripheral spacer means may be used to space the coverslip from the support.

The cover may be made, for example, by vacuum forming, injection molding, stamping, cutting or otherwise forming plastic or another material. The interior surface of the cover may be made hydrophobic in order to prevent condensation of vapor from liquids placed in the sample retention means. The depth of the cover can vary from about 1 mm to about 1 cm. It is preferable, according to some embodiments of the invention, to have a cover height of no more than about 5 mm in order that the entire assembly can be placed under many common standard microscope stages for viewing cells. According to some embodiments of the invention, the cover can be a flat microscope coverslip or coverglass. A film or foam outer border can be attached to the coverslip in order that the coverslip contacts the support without contacting the biological specimen. A single cover which attaches over all the sample retention means may be provided or individual covers with resealable pressure sensitive adhesive borders can be used to enclose individual sample retention means.

According to some embodiments of the invention, an assembly is provided and includes a coverslip, and the closure means is used to resealably seal both a cover and the coverslip to the support. According to some embodiments of the invention, a microbiological assembly is provided wherein the closure means comprises a patterned layer of an adhesive material disposed on the sealing surface of the support and the closure means is adapted to seal the coverslip to the support surface after the cover and the support surface are adhered together and then physically separated from one another. According to such embodiments of the invention, the patterned layer of adhesive material preferably remains substantially intact and adhered to the support surface after the cover is adhered to the support surface and then physically separated from the support surface.

According to embodiments of the invention, the sample retention means may be created by placing films and or foams of from about 5 microns to about 1 mm in thickness on the support. The upper surface of the film or foam forming the sample retention means is either naturally hydrophobic or coated with a non-wettable hydrophobic coating which repels aqueous-based samples and keeps samples in multiple sample retention means separate. The same or a different material as the hydrophobic material may be coated on a portion of the base to provide a writing area which is absorptive and receptive to marking materials and is furthermore resistive to a variety of laboratory solvents, reagents, stains and chemicals. According to some embodiments of the invention, the device may be a glass microscope slide with hydrophobic delimited areas which create both sample retention means and a marking surface.

The size of the sample retention means and the number of sample retention means per device may vary. According to some embodiments of the invention, a standard 1 inch by 3 inch glass microscope slide having a screen printed hydrophobic patterned layer formed thereon may comprise 96 sample retention means, wells or chambers, or more. In addition to separate wells or chambers, wells or chambers can be configured to permit selective exchange of fluids between other selected wells or chambers. For example, a printed hydrophobic layer defining multiple sample retention wells can have a channel connecting two or more of the wells together, which may be done by printing a microporous matrix having pore sizes of from about 1 micron to about 20 microns directly on top of a hydrophobic patterned layer.

The sample retention means may comprise a well having at least one side comprised of clean glass or a glass or plastic material coated with a silane or other chemical or biological material to enhance attachment of cells and to enhance tissue and cell growth. In addition, sample retention wells may be printed with alternating hydrophilic and hydrophobic micron line patterns to increase growth and differentiation of particular cell types.

According to some embodiments of the invention, the sample retention means may comprise wells formed by a printed layer, wells formed into the support, porous patches or plugs disposed on the support, electrically charged regions such as electrets, or reservoirs defined by a patterned layer, for example, a die-cut material layer.

According to embodiments of the invention, a reservoir for a humidifying fluid may be provided within the assembly to protect sample retained in the sample retention means from drying.

According to embodiments of the invention, a method of examining a biological culture is provided wherein a microbiological assembly according to the invention is used to culture a retained biological sample within said sample retention means. A removable cover is resealably sealed to the support surface with the closure means disposed between the sealing surface of the cover and the sealing surface of the support. After a period of culture production, the cover is physically separated from the support. Then, the sample retention means is sealed with a coverslip using the same resealable sealant used to seal the cover to the support. Upon physical separation of the cover from the support surface, the closure means may preferably remain attached to the sealing surface of the support. According to some embodiments of the invention, the closure means may comprise a material that generates an electric or a magnetic force and which is disposed on (1) the sealing surface of the support, (2) the sealing surface of the cover, and (3) a sealing surface of the coverslip.

The following are exemplary uses of the present invention:

1. Cell Cultures

A. Cells may be cultured in individual retaining means, for example, wells on a microscope slide assembly according to embodiments of the invention. Multiple wells allow the use of replicates, a variety of different cell types, or a variety of different culture media contents.

B. Feeder cells may be cultured in conjunction with a dependent cell type, for example, embryonic stem cell cultures. The two cell types may be placed in adjacent wells and allowed to attach. Unattached cells are removed and the medium is then drawn together between the two wells. The feeder cells will then condition the medium of the dependent cell line. At the conclusion of culture production the dependent cells may be viewed or collected independently of the feeder cells.

C. Tissue/organ modeling—By printing complex patterns on the assembly support, cells may be induced to attach in predetermined patterns. These patterns may facilitate the flow of medium through the culture to enhance cell growth and differentiation or the harvest of cell products. The patterns may direct the placement of two or more different cell types to facilitate their biological interaction, as in a liver or other organ.

D. Embryo culture—The culture of individual small pieces of tissue or early embryos can be carried out in a very small defined area on the assembly. This will allow easy location of the embryo or tissue without having to search a large area of culture surface. Multiple treatment and replicates can be carried out on a single slide with multiple wells.

2. Histology

Cultured cells or small tissue sections can be attached to wells for examination using histological, histochemical or immunohistochemical methods. These techniques sometimes use reagents that are expensive or in limited supply. The small volumes required to fill the wells reduce reagent volume requirements significantly.

3. Chemistry

A. The sample retention means of the assembly may be a well which can be used as a chemical reactor. A surface of the well may be coated with one reagent, as in an ELISA test, or reactions may be conducted using solely solution chemistry. Multiple wells allow multiple reactions to be carried out. Small volume wells such as achieved by screen printing a hydrophobic ink layer may reduce the use and waste of costly or limited reagents. For enzyme reactions with limited amount of enzyme or reactant (as with assays of small amounts of tissue), reaction kinetics are improved in a small volume. The products can then be detected by chemical (or enzymatic) amplification reactions or by detection of a radioactive product.

B. The use of small volumes (from about 0.5 $\mu$l to about 200 $\mu$l) is particularly cost-effective where very expensive enzymes are utilized in the reaction. Many laboratories simultaneously run 20 to 50 separate reactions in an experiment. Reagents for this volume typically cost from $10 to about $15 per reaction; therefore, reducing the reaction volume 10 to 100-fold can provide significant savings.

C. Patterns may be employed on the support surface to influence an ordered sequence of chemical reactions. Assemblies according to embodiments of the present invention allow for flexibility in the number and size of sample retention means and permit sample retention means to be connected to each other for reagent or specimen transfer or chemotaxis between wells if desired. Since the size of wells can be customized for particular assays reagent costs can be minimized.

The present invention also finds use in a wide range of other applications in the biological, clinical, and chemical fields, particularly in applications involving eukaryotic cells, plant cells, tumor cells, bacteria, viruses, sperm, blood, urine, and other chemicals.

The flexibility, disposability, and low cost of the assemblies according to the present invention should render new capabilities to studies involving cell culture. The present invention enables scientists and clinicians involved in cell culture research to design novel experiments in the field of biology including microbiology, biochemistry, and human diseases, and to lead to new achievements in the fields of cell structure, cell adhesion, cell-to-cell interaction, cell migration, cytotoxicity, and many other related areas. The present assemblies also find application in the field of medical diagnostics by providing for many simultaneous low volume, low cost assays.

Figure 2:
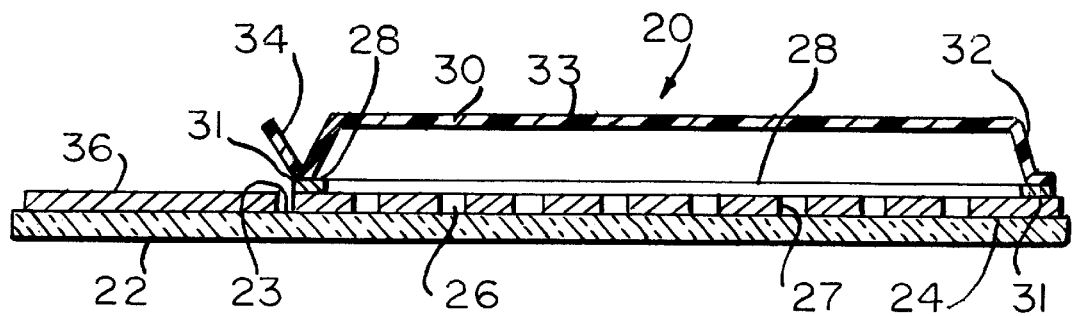
FIG. 2 is a cross-sectional view taken along line 2—2 of FIG. 1.

The assemblies of the invention will now be described with reference to the drawings. FIGS. 1 and 2 show a microbiological assembly 20 according to embodiments of the present invention. The assembly 20 comprises a support 22, which may be a standard 1 inch by 3 inch microscope slide, having a top surface 23 and a patterned layer 24 of a printed hydrophobic ink coated on a portion of the top surface 23. A plurality of sample retention wells 26 are provided on the support 22 and are defined by the top surface 23 of the support 22 and sidewalls 27 comprising part of the patterned layer 24. A resealable pressure sensitive adhesive layer 28 is provided along the periphery of the top surface 23 on the patterned layer 24 and resealably seals a cover 30 to the support 22. The cover 30 may be made of a transparent plastic material and includes a sealing surface 31, sidewall portions 32, a top portion 33, and a release tab 34. The support 22 also includes a surface portion coated with a markable printed coating 36.

Figure 3:
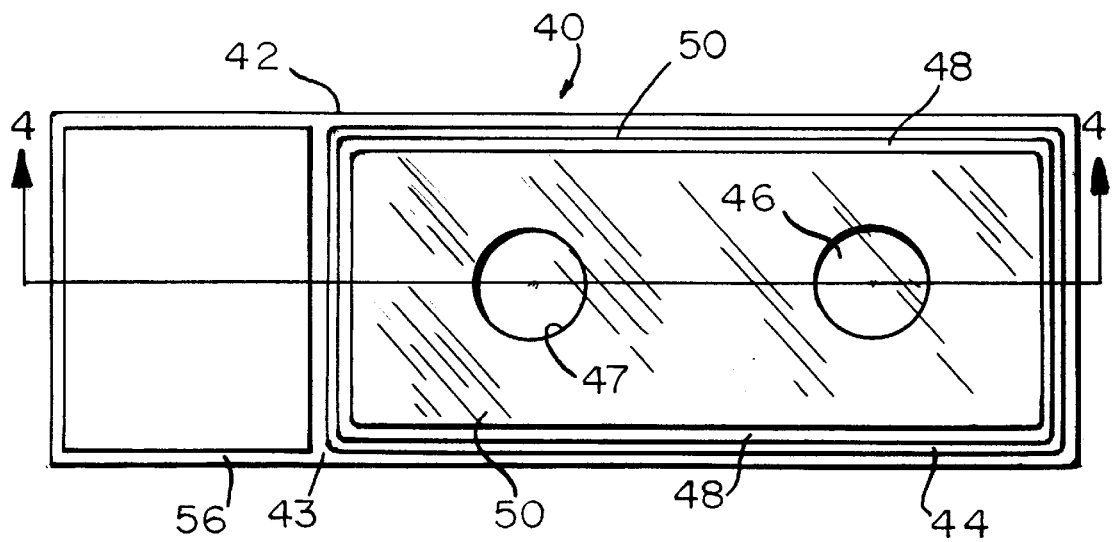
FIG. 3 is a top plan view of another microbiological assembly according to embodiments of the present invention.
Figure 4:
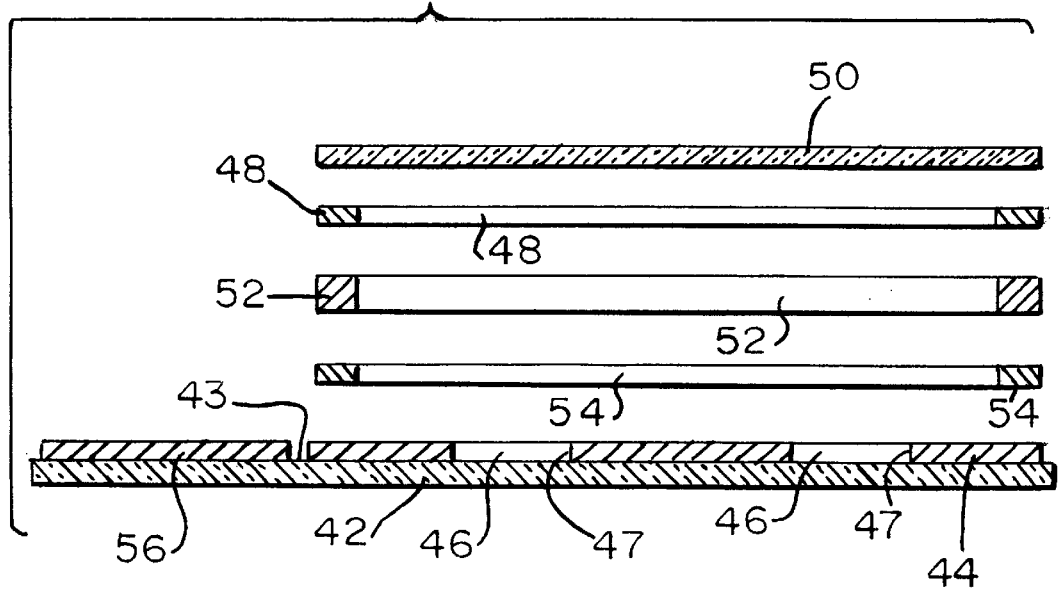
FIG. 4 is a cross-sectional view taken along line 4—4 of FIG. 3, partially exploded.

FIGS. 3 and 4 show another microbiological assembly 40 according to embodiments of the invention. The assembly 40 comprises a support 42 having a top surface 43 and a patterned layer 44 of a printed hydrophobic ink coated on a portion of the top surface 43. A plurality of sample retention wells 46 are provided on the support 42 and are defined by the top surface 43 of the support 42 and sidewalls 47 comprising part of the patterned layer 44. A resealable pressure sensitive adhesive layer 54 is provided along a peripheral portion of the top surface 43 on the patterned layer 44. The resealable adhesive layer 54 resealably seals a die-cut spacer 52 to the printed layer 44 on the support 42. The spacer 52 is sealed to a cover 50 with an adhesive layer 48. The adhesive layer 48 may or may not comprise a resealable pressure sensitive adhesive layer. The cover 50 may be made of a transparet glass material. The support 42 also includes a surface portion coated with a markable printed coating 56.

Figure 5:
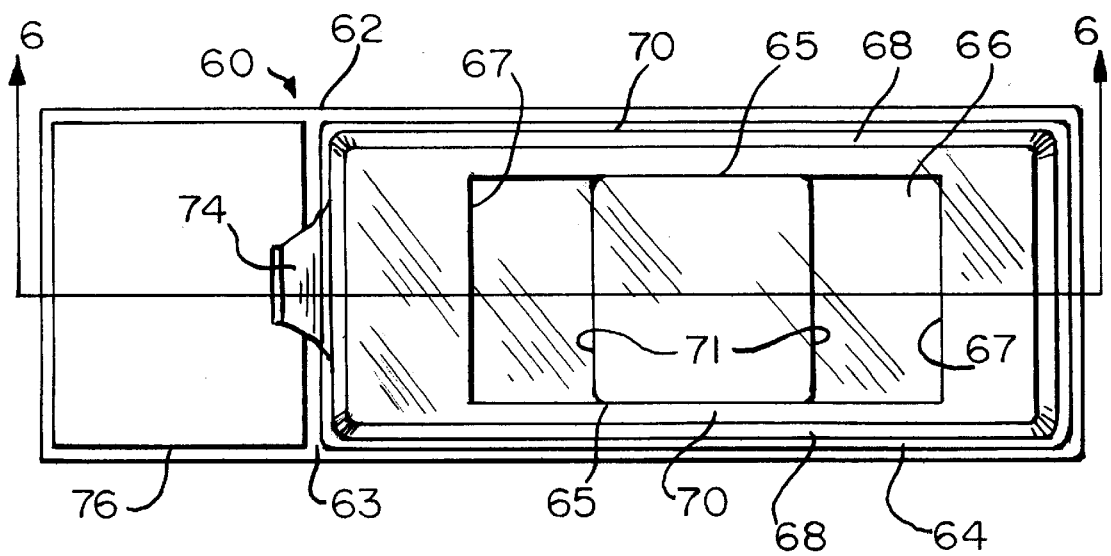
FIG. 5 is a top plan view of another microbiological assembly according to embodiments of the present invention.
Figure 6:
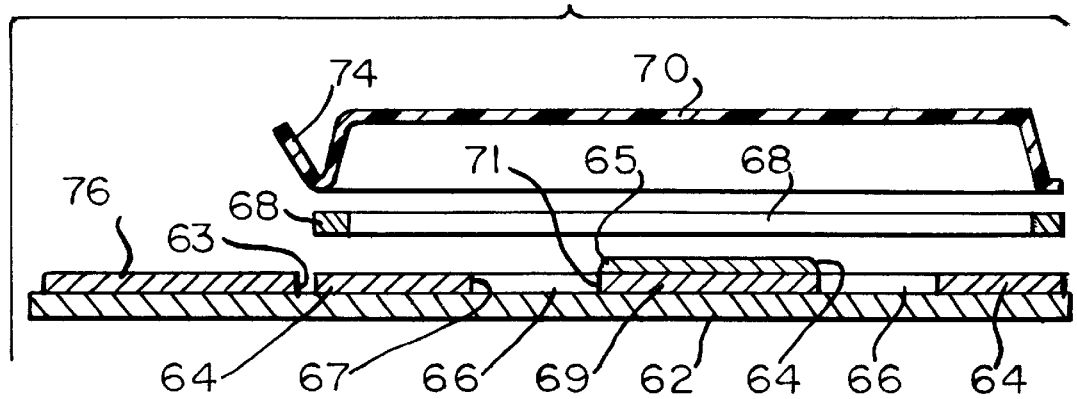
FIG. 6 is a cross-sectional view taken along line 6—6 of FIG. 5, partially exploded.

FIGS. 5 and 6 show another microbiological assembly 60 according to embodiments of the present invention. The assembly 60 comprises a support 62 having a top surface 63 and a patterned layer 64 of a printed hydrophobic ink coated on a portion of the top surface 63. Two sample retention wells 66 are provided on the the support 62. The sample retention wells 66 are defined by the top surface 63 of the support 62, sidewalls 67 which comprise part of the patterned layer 64, and sidewalls 71 of a porous or semipermeable barrier 69 that separates the two wells 66 and sample contained therein. The barrier 69 may provide for the selective exchange of gases, liquids, nutrients, cell products, reaction products or cells between the two wells 66, as described, for example, in U.S. Pat. No. 5,503,803 to Brown, which is incorporated in its entirety herein by reference. According to some embodiments of the invention, one of the two wells 66 is used as a sample retention well and the other of the two wells 66 may be used as a media exchange or nutrient supply well. As shown in FIG. 6, the barrier 69 has first been disposed on the top surface 63 of the support 62, and then the patterned layer 64 has been printed on top of the support 62 and the barrier 69. Thus, the barrier 69 is coated with the printed layer 64, and sidewalls 65 of the printed coating on the barrier 69 also help to retain sample or exchange materials in the respective wells. A resealable pressure sensitive adhesive layer 68 is provided along a peripheral portion of the top surface 63 on the patterned layer 64. The resealable pressure sensitive adhesive layer 68 resealably seals a cover 70 to the patterned layer 64 on the support 62. The cover 70 may be made of a transparent plastic material and includes a pry tab 74 used to release the cover 70 from the coated support. Support 62 also includes a surface portion coated with a markable printed coating 76.

Figure 7:
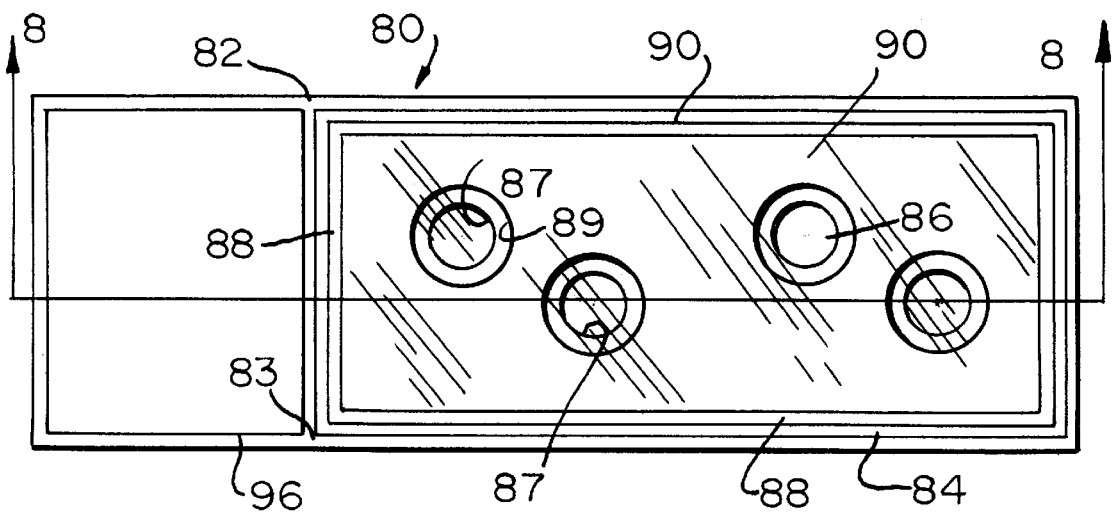
FIG. 7 is a top plan view of another microbiological assembly according to embodiments of the present invention.
Figure 8:
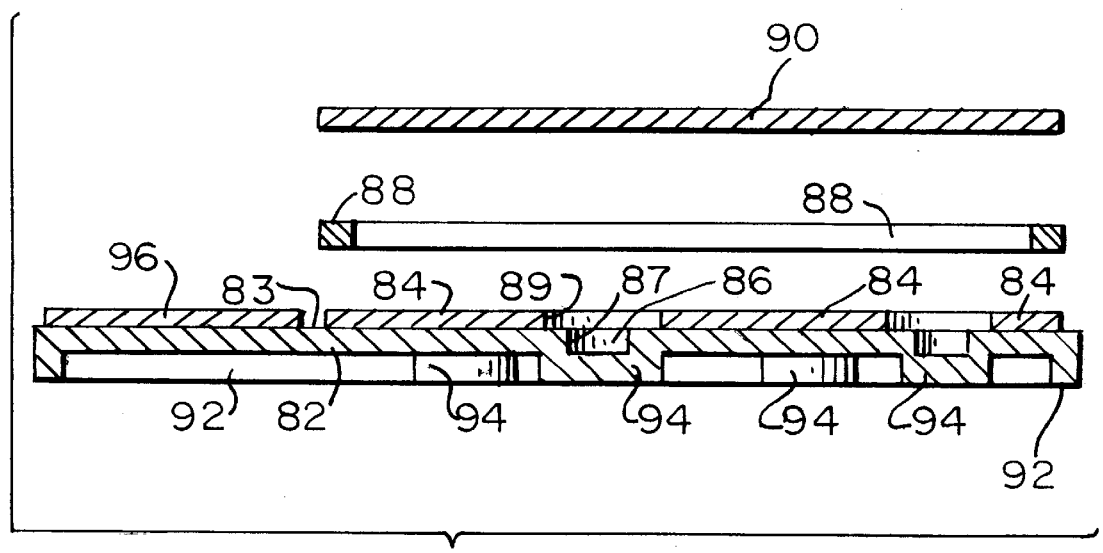
FIG. 8 is a cross-sectional view taken along line 8—8 of FIG. 7, partially exploded.

FIGS. 7 and 8 show another microbiological assembly 80 according to embodiments of the invention. The assembly 80 comprises a support 82 comprising a molded plastic material. The support 82 has a top surface 83 and a patterned layer 84 of a printed hydrophobic ink coated on a portion of the top surface 83. A plurality of sample retention wells 86 are provided and are defined by portions 94 of the support which are depressed relative to the planar top surface 83 of the support 82. The depressed portions 94 of the support 82 define sidewalls 87 of the sample retention wells 86. The molded support 82 is also provided with a rim 92 which provides structural integrity to the support 82 and allows the support to be laid flat on a surface such as the viewing platform of a microscope. The patterned layer 84 includes sidewalls 89 that surround the sample retention wells 86 at the top of the wells. The sidewalls 89 and the uncoated portions of the top surface 83 within the sidewalls 89 may further define the sample retention wells 86. A resealable pressure sensitive adhesive layer 88 is provided along a peripheral portion of the top surface 83 on the patterned layer 84. The resealable adhesive layer 88 resealably seals a cover 90 to the printed layer 84 on the support 82. The cover 90 may be made of a transparent glass material. The support 82 also includes a surface portion coated with a markable printed coating 96.

Figure 9:
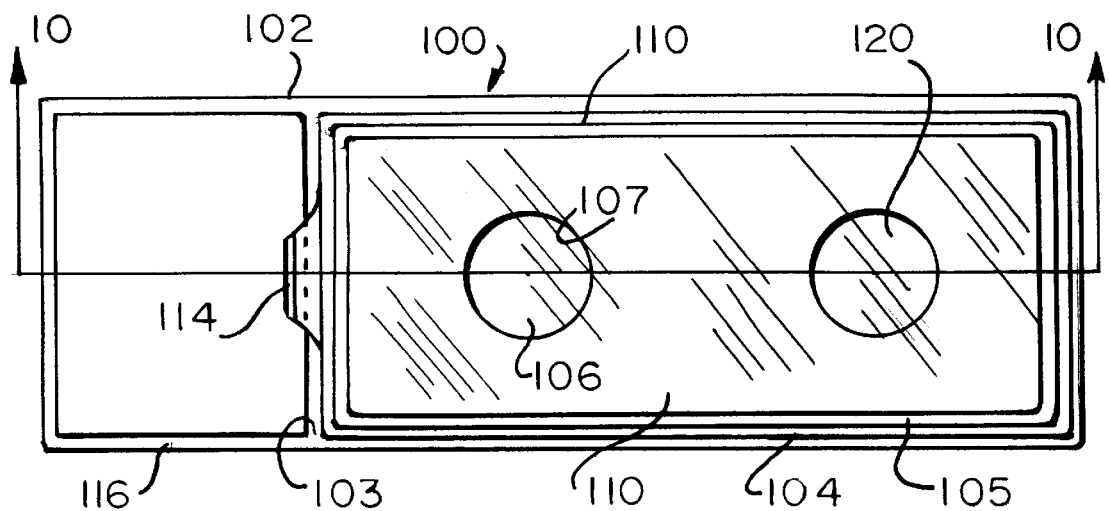
FIG. 9 is a top plan view of another microbiological assembly according to embodiments of the present invention.
Figure 10:
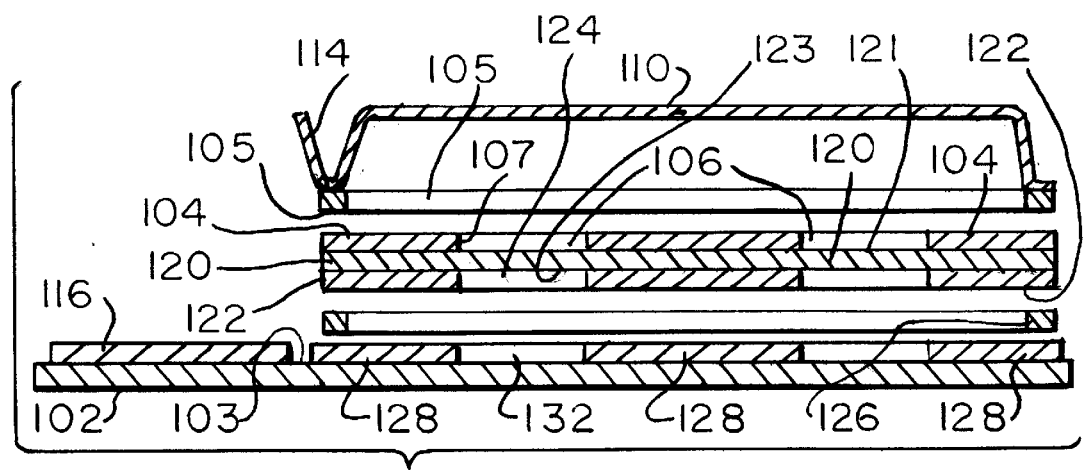
FIG. 10 is a cross-sectional view taken along line 10—10 of FIG. 9, partially exploded.

FIGS. 9 and 10 show another microbiological assembly 100 according to embodiments of the invention. The assembly 100 comprises a support 102 having a top surface 103 which is provided with a patterned layer 128 of a printed hydrophobic ink coated on a portion of the top surface 103. A plurality of sample retention wells 106 are provided between the support 102 and a cover 110. The sample retention wells 106 are defined by a three-layer intermediate structure comprising a porous or semi-permeable membrane 120 having a printed ink coating 104 on a top surface 121 thereof and a printed ink coating 122 on a bottom surface 123 thereof. The wells 106 are defined by the top surface 121 of the membrane 120 and by sidewalls 107 comprised of the printed layer 104. Beneath the sample retention wells 106 and opposite the membrane 120, wells 124 are provided in the printed layer 122 and wells 132 are provided in the printed layer 128. The wells 124 and 132 may together or independently comprise a media exchange or nutrient supply well. The membrane 120 may provide for the selective exchange of gases, liquids, nutrients, cell products, reaction products or cells between the sample retention wells 106 and the underlying wells 124 and/or 132. An adhesive layer 126 is provided along a peripheral portion of the top surface 103 on the patterned layer 128. The adhesive layer 126 may comprise a resealable adhesive, for example, a pressure sensitive adhesive. The adhesive layer 126 adheres the three-layer intermediate structure comprising membrane 120 and printed layers 104 and 122 to the coated top surface of the support 102. On the top side of the three-layer structure, opposite the adhesive layer 126, another adhesive layer 105 is provided. The adhesive layer 105 may comprise a permanent or resealable pressure sensitive adhesive which adheres the three-layer structure to the cover 110. The cover 110 may be made of a transparent plastic material and comprises a pry tab or release lever 114 for releasing the cover 110 from the intermediate, sample well-containing three-layer structure. The support 102 also includes a surface portion coated with a markable printed coating 116.

Figure 11:
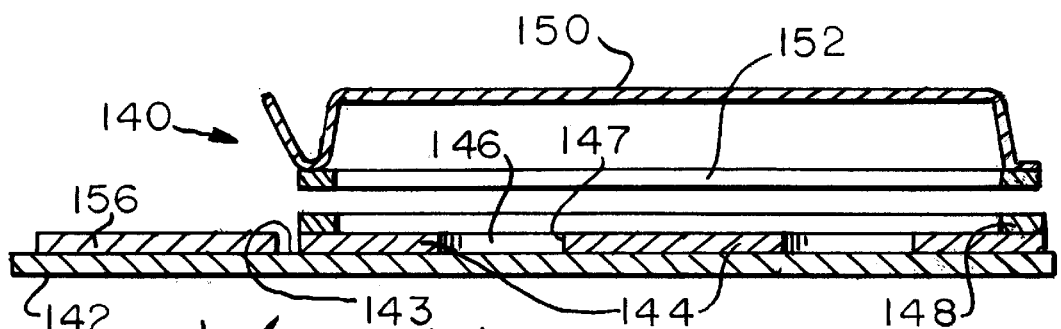
FIG. 11 is a cross-sectional view of another microbiological assembly according to embodiments of the present invention, partially exploded.

FIG. 11 shows yet another microbiological assembly 140 according to embodiments of the present invention. The assembly 140 comprises a support 142 having a top surface 143 and a patterned layer 144 of a printed hydrophobic ink coated on a portion of the top surface 143. A plurality of sample retention wells 146 are provided on the support 142 and are defined by the top surface 143 of the support 142 and sidewalls 147 comprising part of the patterned layer 144. The closure means comprises a patterned layer 148 of a magnetic particle-loaded resin or polymer mounted along the periphery of the top surface 143 on the patterned layer 144, and a patterned layer 152 of a magnetic particle-loaded resin or polymer mounted along the periphery or sealing surface of a cover 150. The layer 148 is permanently adhered to the coated support and the layer 152 is permanently adhered to the cover. The layers 148 and 152 exert attractive forces toward each other and when brought together resealably seal the cover 150 to the coated support 142. The cover 30 may be made of a transparent plastic material and may include a release tab 15 1. The support 142 also includes a surface portion coated with a markable printed coating 156. According to other embodiments of the invention, the layers 148 and 152 may instead comprise electret materials, for example, polymeric electret layers.

Figure 12:
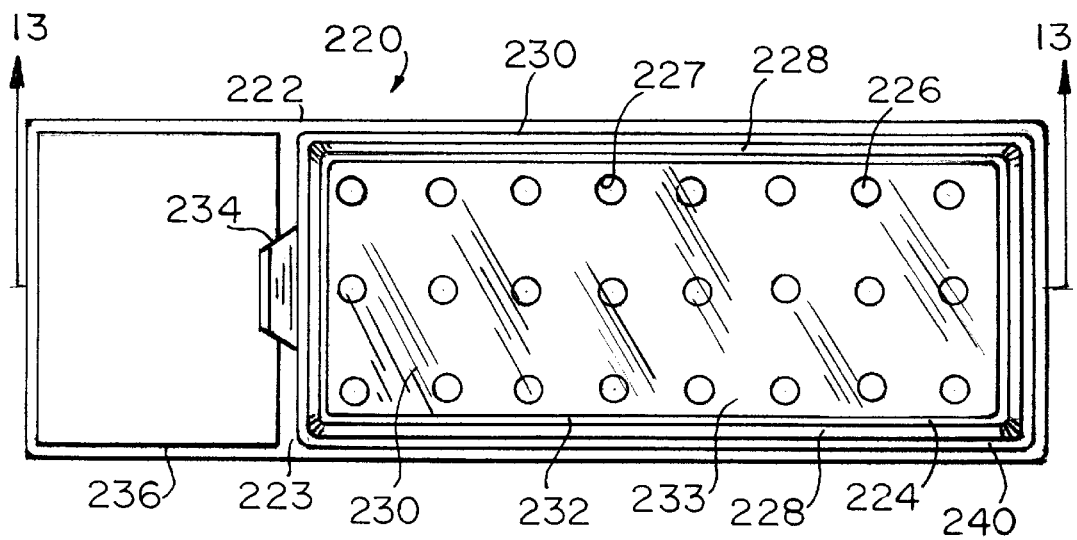
FIG. 12 is a top plan view of another microbiological assembly having a friction-fit closure means according to embodiments of the present invention.
Figure 13:
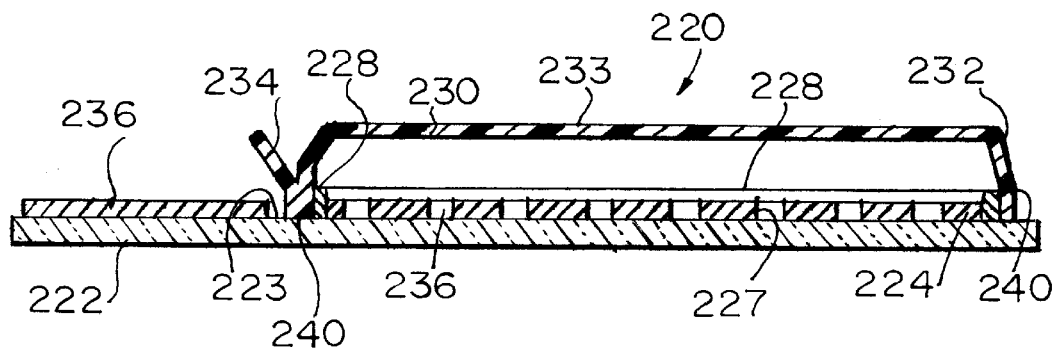
FIG. 13 is a cross-sectional view taken along line 13—13 of FIG. 12.

FIGS. 12 and 13 show a microbiological assembly 220 according to embodiments of the present invention. The assembly 220 comprises a support 222, which may be a standard 1 inch by 3 inch microscope slide, having a top surface 223 and a patterned layer 224 of a printed hydrophobic ink coated on a portion of the top surface 223. A plurality of sample retention wells 226 are provided on the support 222 and are defined by the top surface 223 of the support 222 and sidewalls 227 comprising part of the patterned layer 224. A protruding ridge-forming member 228 is provided and protrudes from along the periphery of the top surface 223 on the support 222. A cover 230 is provided having a ridge-engaging peripheral lower sidewall 240 that fits over the ridge member 228 formed on the support 222. The inner surface of the lower sidewall 240 frictionally engages the ridge member 228 and holds the cover 230 by frictional forces on the support, covering the sample retention wells 226 and forming a resealable closure means. The cover 230 may be repeated removed from the support and resealed to the support, each time forming a leak-proof, substantially liquid-impermeable seal. The cover 230 may be made of a transparent plastic material and also includes sidewall portions 232, a top portion 233, and a release tab 234. The support 222 also includes a surface portion coated with a markable printed coating 236.

COMPARATIVE EXAMPLES AND EXAMPLES

The invention may be illustrated with reference to the following Examples of the invention and Comparative Examples. For reasons which will become apparent below, the Comparative Examples were first tested and then compared to Examples according to the present invention.

Comparative Examples 1 and 2

In Comparative Examples 1 and 2 below, ten commercially available four-chamber SuperCell™ devices (Erie Scientific Company, Portsmouth, N.J.) believed to be made according to the teachings of U.S. Pat. No. 5,571,721 to Turner, were tested under ambient conditions at 25° C. for their ability to seal and reseal against leakage of aqueous fluids between adjacent sample retention wells defined by a compartment adhered to a slide. The compartment had sidewalls with upper extremities and lower margins, and was adapted to be operatively positioned on the upper surface of the slide. The compartment was held to the slide with an adhesive that released from the slide and remained in contact with the compartment when the compartment was separated from the slide. The adhesive was an ordinary acrylic adhesive, as described in U.S. Pat. No. 5,571,721 to Turner, and was moderately hydrophobic and exhibited little chemical resistance. The adhesive is believed to be designated product number S268 available from Coating Sciences, Inc., Bloomfield, Conn.

The wells were arranged as an array of four wells in a row, long side-by-long side, each well being about 7/8 inch long, about 1/2 inch wide, and about 7/16 inch deep. A removable lid for each device, provided to cover the open tops of the four wells, was discarded. The first and fourth wells were adjacent only to the second and third wells, respectively. The second well was adjacent and between the first and third wells, and the third well was adjacent and between the second and fourth wells.

Comparative Example 1

Aliquots comprising 500 µl of a saturated ascorbic acid solution containing 0.01 percent surfactant TWEEN™ 80 were pipetted into the first and third wells of each device and 200 µl aliquots of a saturated aqueous solution of sodium bicarbonate were pipetted into the second and fourth wells of each device. The inclusion of TWEEN™ 80 lowered the surface tension of the ascorbic acid solution to about that of a typical cell culture media, about 50 dynes/cm. The greater volume of the ascorbic acid solution created a pressure differential between the ascorbic acid solution wells (the first and third wells) and the sodium bicarbonate solution wells (the second and fourth wells). After one hour, in six out of ten devices substantial numbers of $CO_2$ bubbles had formed in the bicarbonate solution at the lower edge of the compartment sidewalls separating the sodium bicarbonate solution wells from adjacent ascorbic acid solution wells.

Comparative Example 2

The ten devices used in Comparative Example 1 were disassembled, rinsed thoroughly with deionized water (DI water), dried, and then reassembled. A ten pound weight was used to apply pressure to the compartment and acrylic adhesive material for ten minutes. Then, 500 µl aliquots of a saturated ascorbic acid solution containing 0.01 percent surfactant TWEEN™ 80 were pipetted into the first and third wells of each device and 200 µl aliquots of a saturated aqueous solution of sodium bicarbonate were pipetted into the second and fourth wells of each device. After one hour, substantial numbers of $CO_2$ bubbles had formed in all ten of the devices, at the lower edge of the compartment sidewalls separating the sodium bicarbonate solution wells from adjacent ascorbic acid solution wells.

The formation of bubbles in the Comparative Examples indicates leakage and liquid permeability between wells in the multi-well devices. Six of the ten devices in Comparative Example 1 failed to provide a leak-proof original seal as commercially provided. None of the ten devices tested in Comparative Example 2 was resealable. In each of the ten devices tested in Comparative Example 2 the amount of bubbles was significant, indicating major leaks along the tried barriers.

Example 1

The ten devices used in Comparative Example 2 were then disassembled, rinsed thoroughly with deionized water, and dried. Then, for each device a layer of resealable pressure sensitive adhesive was applied according to the present invention. The resealable adhesive was applied from solution to the surface of the existing SuperCell™ acrylic adhesive remaining on the lower margin of the compartment after the compartment was separated from the slide. The resealable adhesive according to the invention was formed from a solution comprising about 50% by weight FC-77 FLUORINERT solvent available from Commercial Chemicals Division, 3M, St. Paul, Minnesota, and about 50% by weight perfluorooctyl acrylate polymer. The resealable adhesive solution was then allowed to dry resulting in a resealable pressure sensitive adhesive coating on the original adhesive of the SuperCell™ device. The devices were then reassembled and a ten pound weight was used to apply pressure to the compartment and resealable adhesive material for ten minutes.

Then, 500 µl aliquots of a saturated ascorbic acid solution containing 0.01 percent surfactant TWEEN™ 80 were pipetted into the first and third wells of each device and 200 µl aliquots of a saturated aqueous solution of sodium bicarbonate were pipetted into the second and fourth wells of each device. After twelve hours, no bubbles had formed at the lower barriers between compartments in any of the ten devices, indicating a leak-proof, liquid impermeable seal.

Example 2

The ten SuperCell™ devices modified according to the invention in Example 1 were then each disassembled and thoroughly rinsed with deionized water. Substantially all of the adhesive from each device was removed. Then, for each device, a layer of resealable pressure sensitive adhesive was applied according to the present invention. The resealable adhesive layer of device had a thickness of about 100 microns and was applied in a pattern matching the lower margins of the sidewalls of the compartment defining the wells. The resealable adhesive layer was applied from solution comprising about 50% by weight perfluorooctyl acrylate polymer, about 50% by weight perfluorooctyl acrylate monomer, and a catalytic amount of a UV-curing catalyst. The resealable adhesive solution was then UV-cured under $N_2$ to form a resealable pressure sensitive adhesive layer according to the present invention. Then, the devices were reassembled and a ten pound weight was used to apply pressure to the compartment and resealable adhesive material for ten minutes.

Then, 500 µl aliquots of a saturated ascorbic acid solution containing 0.01 percent surfactant TWEEN™ 80 were pipetted into the first and third wells of each device and 200 µl aliquots of a saturated aqueous solution of sodium bicarbonate were pipetted into the second and fourth wells of each device. After twelve hours, no bubbles had formed at the lower barriers between compartments in any of the ten devices, indicating a leak-proof, liquid-impermeable seal.

Example 3

The devices used in Example 2 were then disassembled, rinsed thoroughly with deionized water, and reassembled. Then, 500 µl aliquots of a saturated ascorbic acid solution containing 0.01 percent surfactant TWEEN™ 80 were pipetted into the first and third wells of each device and 200 µl aliquots of a saturated aqueous solution of sodium bicarbonate were pipetted into the second and fourth wells of each device. After twelve hours, no bubbles had formed at the lower barriers between compartments in any of the ten devices, indicating a leak-proof, liquid-impermeable resealable seal.

As can be seen from the foregoing Examples 1–3, a resealable, leak-proof and liquid-impermeable seal can be provided according to the present invention whereas these features are not provided by the commercially available SuperCell™ product. The fact that previously failed devices were used in Examples 1–3, the resealable adhesive seal according to the present invention surprisingly and unexpectedly provided a leak-proof, liquid-impermeable and resealable seal when used on a clean slide or over an existing failed adhesive layer.

Although the present invention has been described in connection with preferred embodiments, it will be appreciated by those skilled in the art that additions, modifications, substitutions and deletions not specifically described may be made without departing from the spirit and scope of the invention defined in the appended claims.

What is claimed is:

1. A microbiological assembly comprising a support, resealable closure means, and a cover, said support having a support surface comprising a patterned layer, said support surface comprising a sample retention means, said cover having a sealing surface for contacting said resealable closure means, said resealable closure means being adapted to releasably bond and resealably seal the cover to the support surface and comprising a patterned layer of an adhesive material disposed on either the support surface or the sealing surface, said patterned layer of adhesive material remaining resealable, substantially intact, and disposed on said support surface or sealing surface after adhering the cover to the support surface and then physically separating the cover from the support surface, wherein when said closure means reseals the cover to the support surface a substantially leak-free, liquid impermeable, resealable sealed container is provided having the sample retention means contained therein and said resealed container minimizes contamination and drying of liquid sample retained by the sample retention means.

2. A microbiological assembly as claimed in claim 1 wherein said closure means comprises a pressure sensitive adhesive.

3. A microbiological assembly as claimed in claim 1 wherein said closure means comprises a fluorinated acrylic adhesive.

4. A microbiological assembly as claimed in claim 1 wherein said closure means comprises a pressure sensitive silicone adhesive.

5. A microbiological assembly comprising a support, resealable closure means, and a cover, said support having a support surface comprising a patterned layer, said support surface comprising a sample retention means, said cover having a sealing surface for contacting said resealable closure means, and said closure means comprises a magnetic material disposed on the sealing surface of the cover and on the support surface and is adapted to releasably bond and resealably seal the cover to the support surface, wherein when said closure means seals the cover to the support surface a substantially leak-free sealed container is provided having the sample retention means contained therein and said sealed container minimizes contamination and drying of liquid sample retained by the sample retention means.

6. A microbiological assembly as claimed in claim 5 wherein said closure means comprises a hardenable polymer or resin having magnetic particles dispersed throughout.

7. A microbiological assembly as claimed in claim 6 wherein said hardenable polymer or resin has been substantially hardened from a substantially non-hardened state while a magnetic field was applied to the polymer or resin.

8. A microbiological assembly comprising a support, resealable closure means and a cover, said support having a support surface comprising a patterned layer, said support surface comprising a sample retention means, said cover having a sealing surface for contacting said resealable closure means, and said closure means comprises a material that has been hardened in the presence of an electric field and holds a charge and is adapted to releasably bond and resealably seal the cover to the support surface, wherein when said closure means seals the cover to the support surface a substantially leak-free sealed container is provided having the sample retention means contained therein and said sealed container minimizes contamination and drying of liquid sample retained by the sample retention means.

9. A microbiological assembly as claimed in claim 8 wherein said hardenable material comprises at least one meltable plastic having a dipole moment.

10. A microbiological assembly as claimed in claim 8 wherein said hardenable material comprises at least one member selected from the group consisting of polycarbonate polymers, polypropylene polymers and polystyrene polymers.

11. A microbiological assembly comprising a support, resealable closure means, and a cover, said support having a support surface comprising a patterned layer, said support surface comprising a sample retention means, said cover having a sealing surface for contacting said resealable closure means, and wherein the resealable closure means is disposed between the sealing surface and the patterned layer of the support surface and seals the cover to the patterned layer of the support surface to form a substantially leak-free sealed container which minimizes contamination and drying of liquid sample retained by the sample retention means.

12. A microbiological assembly comprising a support, resealable closure means, and a cover, said support having a support surface comprising a patterned layer of a die-cut material layer and said support surface comprising a sample retention means, said cover having a sealing surface for contacting said resealable closure means, and said closure means is adapted to releasably bond and resealably seal the cover to the support surface, wherein when said closure means seals the cover to the support surface a substantially leak-free sealed container is provided having the sample retention means contained therein and said sealed container minimizes contamination and drying of liquid sample retained by the sample retention means.

13. A microbiological assembly as claimed in claim 12 wherein said die-cut material layer comprises a foam material, the support further comprises a support member, said die-cut foam layer is disposed on a surface of said support member, and said foam material is substantially permanently adhered to the surface of the support member.

14. A microbiological assembly as claimed in claim 12 wherein said support member comprises a microscope slide.

15. A microbiological assembly comprising a support, resealable closure means, and a cover, said support having a support surface having a patterned layer disposed thereon which comprises a printable ink, said support surface comprising a sample retention means, said cover having a sealing surface for contacting said resealable closure means, and said closure means being adapted to releasably bond and resealably seal the cover to the support surface, wherein when said closure means seals the cover to the support surface a substantially leak-free sealed container is provided having the sample retention means contained therein and said sealed container minimizes contamination and drying of liquid sample retained by the sample retention means.

16. A microbiological assembly as claimed in claim 15 wherein the patterned layer of the support surface comprises a printable hydrophobic fluorinated ink.

17. A microbiological assembly as claimed in claim 1 further comprising a coverslip, wherein the closure means comprises a patterned layer of an adhesive material disposed on the support surface and said closure means is adapted to seal the coverslip to the support surface after the cover and the support surface are adhered together by the adhesive material and then physically separated from one another, said patterned layer of adhesive material remaining substantially intact and adhered to the support surface after adhering the cover to the support surface and then physically separating the cover from the support surface.

18. A method of examining a biological culture, said method comprising:

providing a microbiological assembly according to claim 1, retaining a biological sample within said sample retention means, sealing the cover to the support surface with the closure means disposed between the sealing surface and the support surface, physically separating the cover from the support surface, and then sealing at least one of the cover and a coverslip to said support surface with the closure means disposed between the support surface and the cover or a coverslip.

19. A method as claimed in claim 18 wherein, upon physical separation of the cover from the support surface, the closure means remains attached to the support surface, and said coverslip is then attached to the support surface with the resealable closure means disposed between the coverslip and the support surface and sealing the cover to the support surface.

20. A method as claimed in claim 18 wherein said assembly comprises a coverslip, the closure means comprises a material that generates an electric or a magnetic force, the force-generating material is disposed on (1) said support surface, (2) said sealing surface, and (3) a sealing surface of the coverslip, and said method comprises sealing the coverslip to the support surface after sealing the cover to the support surface and then physically separating the cover from the support surface.

21. A method as claimed in claim 18 wherein said closure means comprises a pressure sensitive adhesive.

22. A microbiological assembly comprising a support, resealable closure means, and a cover, said support having a support surface comprising a patterned layer, said support surface comprising a sample retention means, said cover having a sealing surface for contacting said resealable closure means, said resealable closure means being adapted to releaseably bond and resealably seal the cover to the support surface and comprising a first patterned layer of an adhesive material disposed on the support surface and a second patterned layer of an adhesive material disposed on the sealing surface, said first patterned layer of adhesive material remaining resealable, substantially intact, and disposed on said support surface after adhering the cover to the support surface and then physically separating the cover from the support surface, said second patterned layer of adhesive material remaining resealable, substantially intact, and disposed on said sealing surface after adhering the cover to the support surface and then physically separating the cover from the support surface, wherein when said closure means reseals the cover to the support surface a substantially leak-free, liquid impermeable, resealable sealed container is provided having the sample retention means contained therein and said sealed resealed container minimizes contamination and drying of liquid sample retained by the sample retention means.

* * * * *